United States Patent [19]

Konrad et al.

[11] Patent Number: 4,883,656
[45] Date of Patent: Nov. 28, 1989

[54] COMPOSITION AND METHOD FOR THE OXIDATIVE DYEING OF HAIR

[75] Inventors: Eugen Konrad, Darmstadt; Herbert Mager, Fribourg; Axel Hoffmann, Reinheim, all of Fed. Rep. of Germany

[73] Assignee: Wella Aktiengesellschaft, Darmstadt, Fed. Rep. of Germany

[21] Appl. No.: 133,130
[22] PCT Filed: Mar. 12, 1987
[86] PCT No.: PCT/EP87/00144
§ 371 Date: Nov. 12, 1987
§ 102(e) Date: Nov. 12, 1987
[87] PCT Pub. No.: WO87/05801
PCT Pub. Date: Oct. 8, 1987

[30] Foreign Application Priority Data

Mar. 27, 1986 [DE] Fed. Rep. of Germany ....... 3610396

[51] Int. Cl.$^4$ .............................................. A61K 7/13
[52] U.S. Cl. .......................................... 424/70; 8/408; 8/412
[58] Field of Search ....................... 8/408, 412; 424/70

[56] References Cited

FOREIGN PATENT DOCUMENTS 166100 1/1986 European Pat. Off. .
3314565 10/1984 Fed. Rep. of Germany .

Primary Examiner—Ellis P. Robinson
Assistant Examiner—Susan S. Rucker
Attorney, Agent, or Firm—Michael J. Striker

[57] ABSTRACT

A composition and method for the oxidative dyeing of hair based on a combination of coupler substance and developer substance, wherein they contain (A) 5-amino-2-methylphenol as coupler substance and
(B) 4-amino-3-methylphenol and
(C) 1,4-diaminobenzene and/or 2,5-diaminotoluene as developer substances, also in the form of the physiologically compatible salts.

The new composition enables the production of neutral red color shades which are free from yellow and virtually free of blue portions and, in addition to the high dye intensity and brilliance, have an outstanding dye equality with very good absorptive power.

10 Claims, No Drawings

COMPOSITION AND METHOD FOR THE OXIDATIVE DYEING OF HAIR

The subject matter of the invention is a composition for the oxidative dyeing of hair based on a combination of coupler and developer substances, wherein 5-amino-2-methylphenol is used as a coupler substance and 4-amino-3-methylphenol and 1,4-diaminobenzene and/or 2,5-diaminotoluene are used as developer substances.

In the area of hair coloring, oxidative dyestuffs have achieved considerable importance. The dyeing is brought about by means of the reaction of certain coupler substances with certain developer substances in the presence of a suitable oxidizing agent.

There are numerous special requirements for oxidative dyestuffs which are used for dyeing human hair. For example, they must be harmless in toxicological and dermatological respects and must make it possible to achieve the desired intensity of dyeing. Moreover, it is necessary that a wide assortment of various color shades can be achieved by means of combining suitable developer and coupler substances. In addition, a favorable light fastness, fastness to permanent waving and acids and rubbing fastness are required of the hair colorings which can be achieved. But, in every instance, such hair colorings must remain stable over a period of at least 4 to 6 weeks without being influenced by light, chemical agents or friction.

1,4-diaminobenzene, 2,5-diaminotoluene, 2,5-diaminobenzyl alcohol and 4-aminophenol are preferably used as developer substances. 4-aminophenol is used chiefly for producing fashionable shades, wherein orange is produced in combination with the coupler substance 5-amino-2-methylphenol, a violet-tinted red is produced with the coupler substance 1-naphthol, and a violet is produced with the coupler substance m-phenylenediamine and its derivatives. It is a great disadvantage that these dye shades are not neutral reds, but rather always contain blue or yellow portions. Another significant disadvantage results when these dye shades are mixed with natural shades based on 1,4-diaminobenzene or 2,5-diaminotoluene. That is, the expected dyeing result located between the natural shade and the admixed red shade is not obtained here, rather a completely unexpected violet dye shade is obtained. This violet dye shade is caused by means of the reaction of the p-diamine, for example, the 1,4diaminobenzene, with 1-naphthol and with m-phenylenediamine or its derivatives.

Oxidizing hair dyeing compositions are described in DE-PS 1 143 605 which contain 5-amino-2-methylphenol in combination with aromatic 1,4-diamines as coupler substances. However, these hair dyeing compositions only provide violet dye shades which can be used in the red shade area only to a very limited degree because of their blue-tinted dyeing character.

Although the developer substance 4-amino-3-methylphenol is frequently mentioned in publications on hair dyeing, it has achieved very little importance, if any, in practice. Thus, 4-amino-3-methylphenol with 5-amino-2-methylphenol as coupler only provides a brick-red which is weak in color.

Therefore, it is the object of the invention to provide a hair dyeing composition and a method for dyeing hair in which the aforementioned disadvantages are avoided.

It has been found in a surprising manner that this object is met to an outstanding degree by compositions for the oxidative dyeing of hair based on a combination of coupler substances and developer substances which are characterized in that they contain (A) 5-amino-2-methylphenol as coupler substance and
(B) 4-amino-3-methylphenol and
(C) 1,4-diaminobenzene and/or 2,5-diaminotoluene as developer substances, also in the form of the physiologically compatible salts.

Chloride, sulfate, phosphate, acetate, propionate, lactate or citrate, for example, are taken into consideration as physiologically compatible salts with inorganic or organic acids. They can also be used in the form of their salts with bases, for example, as alkaliphenolates, insofar as the dye substances contain aromatic OH groups.

Whereas a certain surplus quantity of 4-amino-3-methylphenol relative to 1,4-diaminobenzene and/or 2,5-diaminotoluene proves advantageous with the developer substances, the coupler substance 5-amino-2-methylphenol can be contained in an equimolar ratio, or in a greater or lesser quantity, with reference to the developer substances.

In the hair dyeing compositions, according to the invention, the 5-amino-2-methylphenol should be contained in a quantity of 0.1 to 5.0 percent by weight, preferably 0.2 to 3.5 percent by weight.

The 4-amino-3-methylphenol should be contained in a quantity of 0.1 to 4.0 percent by weight, preferably 0 2 to 3.0 percent by weight, while the 1,4-diaminobenzene and/or the 2,5-diaminotoluene is contained in a total quantity of 0.1 to 2.0 percent by weight, preferably 0.2 to 1.0 percent by weight.

Neutral red dye shades, particularly fashionable shades, which are free of yellow portions and virtually free of blue portions, can be achieved with the new coupler substance/developer substance combination.

In addition to the high intensity of color, the high brilliance of the shades obtained, which appear particularly when dyeing pigmented natural hair, are surprising. Another advantage is the outstanding dyeing equality of the red shades and the very good absorptive power on the porous ends of the hair. In this respect, the dye combination according to the invention is clearly superior to hair dye compositions with red nitro dyestuffs, for example, 2-nitro-1,4-diaminobenzene.

The statements above show that the hair colorings which can be achieved with the combination of substances according to the invention produce an unexpected color-pure red shade which is only achieved in the simultaneous presence of the two developer substances (B) and (C) and 5-amino-2-methylphenol (A) as coupler substance.

The system, according to the invention, consisting of coupler substance (A) and the two developer substances (B) and (C), is very manageable and easy to handle in the practice of dyeing. In addition, the substances of the components (A), (B) and (C) are manufactured on a commercial scale and are accordingly economical raw materials.

Further, both the 5-amino-2-methylphenol and the 4-amino-3-methylphenol are advantageous in a toxicological respect. Accordingly, because of the combination of coupler and developer substance according to the invention, the dyestuffs 4-aminophenol, 1-naphthol, m-phenylenediamine and 2,4-diaminophenol ether, which are not completely harmless physiologically, can be dispensed with.

Moreover, a wide assortment of various fashionable shades which cannot be produced with 4-aminophenol as developer, particularly a highly fashionable incandescent red with particular brilliance, are accessible with the new combination of coupler and developer substance.

However, the possibilities for dyeing are not restricted only to the production of intensive, highly fashionable dye shades. The fashionable dyeing character can be modified so as to produce a natural-looking color shade by means of the addition of suitable coupler substances as shaders, for example, the coupler substance 4-(2'-hydroxyethyl)amino-1,2-methylenedioxybenzene. Further, conventional coupler substances can, of course, also be used in the new hair dyeing compositions in addition to component (A), for example, 4-amino-1,2methylenedioxybenzene, 4-hydroxy-1,2-methylenedioxybenzene, resorcinol, 4-chlororesorcinol, 2-methylresorcinol, 3-aminophenol, sesamol, and 3,4-methylenedioxyaniline.

For the purpose of shading, additional known developer substances can be used in addition to components (B) and (C), for example, 2,5-diaminobenzyl alcohol.

The known developer and coupler substances can be contained in the hair dye compositions individually or in a mixture.

The total quantity of the coupler substance/developer substance combination in the hair dye compositions described here should be approximately 0.3 to 6.0 percent by weight, preferably 0.4 to 5.0 percent by weight.

In addition, the hair dye composition of this application can contain other dyeing components, for example, 6-amino-2-methylphenol and 2-amino-5-methylphenol, as well as other conventional direct-dyeing dyestuffs, for example, triphenylmethane dyestuffs, such as Diamond Fuchsine (C.I. 42 510) and Leather Ruby HF (C.I. 42 520), aromatic nitro dyestuffs, such as 1,4-diamino-2-nitrobenzene, 2-amino-4-nitrophenol, 2-amino-5-nitrophenol and 2-amino-4,6-dinitrophenol, azo dyestuffs such as Acid Brown 4 (C.I. 14 805) and Acid Blue 135 (C.I. 13 385), anthraquinone dyestuffs such as Disperse Red 15 (C.I. 60 710) and Disperse Violet 1 (C.I. 61 100), and 1,4,5,8-tetraaminoanthraquinone and 1,4-diaminoanthraquinone.

Moreover, other conventional cosmetic ingredients can also be present in the hair dye composition, for example, antioxidants such as ascorbic acid, resorcinol or sodium sulfite, perfume oils, complexing agents, wetting agents, emulsifying agents, thickeners, hair care materials, etc.

The preparation form can be a solution, for example, particularly an aqueous or aqueous-alcoholic solution. However, creams, gels or emulsions are particularly preferred as preparation forms.

Its composition is a mixture of dyestuff components with the usual ingredients for such preparations.

The usual ingredients in solutions, creams, emulsions or gels are, for example, solvents such as water, lower aliphatic alcohols, for example, ethanol, propanol and isopropanol, as well as polyhydric alcohols such as ethylene glycol, 1,2-propylene glycol and glycerine, wetting agents or emulsifying agents from the classes of anionic, cationic, amphoteric or nonionogenic surface-active substances such as fatty alcohol sulfates, alkyl sulfonates, alkylbenzene sulfonates, fatty acid taurides, alkyltrimethyl ammonium salts, alkylbetaines, oxethylated fatty alcohols, oxethylated nonylphenols, fatty acid alkanol amides or oxethylated fatty acid esters; also thickeners such as higher fatty alcohols, bentonite, starch, polyacrylic acid, cellulose derivatives, alginates, vaseline, paraffin oil and fatty acids, as well as hair care materials such as lanolin derivatives, cholesterin, pantothenic acid and betaine. The aforementioned components are used in the amounts which are conventional for such purposes, for example, the wetting agents and emulsifying agents can be contained in the preparations in concentrations of approximately 0.5 to 30 percent by weight, while the thickeners can be contained in the preparations in quantities of approximately 0.1 to 25 percent by weight.

According to the composition, the hair dye compositions, according to the invention, can react in a slightly acidic, neutral or alkaline manner. In particular, they have a pH value in the alkaline range between 8.0 and 11.5, wherein they are preferably adjusted with ammonia. However, organic amines, for example, monoethanolamine and triethanolamine, or inorganic bases such as sodium hydroxide and potassium hydroxide, can also be used.

The hair dyeing compositions according to the invention based on the coupler substance/developer substance combination described above enable hair dyeing with outstanding evenness and fastness characteristics They can be removed again with reducing agents With respect to the dyeing possibilities, the hair dyeing compositions, according to the invention, depending on the type and composition, offer a wide assortment of different fashionable and semi-fashionable dye shades which represent a substantial enrichment and qualitative improvement of the previously known dyeing methods.

When applied for the purpose of the oxidative dyeing of hair, the aforementioned hair dye composition is mixed with an oxidizing agent immediately prior to use and a quantity of this mixture sufficient for the hair treatment, generally approximately 60 to 200 g, according to the fullness of the hair, is applied to the hair. For the most part, hydrogen peroxide, or its addition compounds in urea, melamine or sodium borate in the form of 3 to 12 percent aqueous solutions, come under consideration as oxidizing agents for the development of the hair coloring. If a 6 percent hydrogen peroxide solution is used as oxidizing agent, then the weight ratio between the hair dye composition and the oxidizing agent is 5:1 to 1:2, but preferably 1:1. Larger quantities of oxidizing agent are used in the hair dye composition chiefly in higher dyestuff concentrations or when a more intensive bleaching of the hair is intended. The mixture is allowed to act on the hair at 15° to 50° C. for approximately 10 to 45 minutes, preferably 30 minutes; the hair is then rinsed with water and dried. The hair is washed with a shampoo after this rinse, if necessary, and possibly rerinsed with a weak organic acid such as citric acid or tartaric acid. The hair is then dried.

The subject matter of the invention is explained in more detail in the following examples.

EXAMPLES

EXAMPLE 1

Hair dye solution

| | |
|---|---|
| 3.0 g | 5-amino-2-methylphenol |
| 2.0 g | 4-amino-3-methylphenol |
| 0.3 g | 1,4-diaminobenzene |
| 0.8 g | sodium hydroxide, solid |
| 0.5 g | sodium sulfite |
| 10.0 g | isopropanol |
| 10.0 g | lauryl alcohol diglycolethersulfate sodium salt, 28 percent aqueous solution |
| 10.0 g | ammonia, 25 percent aqueous solution |
| 63.4 g | water |
| 100.00 g | |

50 g of the hair dye composition described above is mixed with 50 ml hydrogen peroxide solution (6 percent) shortly before using and the mixture is then applied to grayed human hair. After it is allowed to act for 30 minutes at 40° C., the hair is rinsed with water and dried. The hair has taken on an intensive neutral red shade which is free of yellow and violet portions.

Example 2

Hair dye composition in gel form

| | |
|---|---|
| 1.5 g | 5-amino-2-methylphenol |
| 0.9 g | 4-amino-3-methylphenol |
| 0.6 g | 2,5-diaminotoluene sulfate |
| 0.4 g | sodium hydroxide, solid |
| 0.6 g | ascorbic acid |
| 7.0 g | isopropanol |
| 15.0 g | oleic acid |
| 10.0 g | ammonia, 25 percent aqueous solution |
| 64.0 g | water |
| 100.0 g | |

Shortly before use, 50 g of this hair dye composition is mixed with 50 ml hydrogen peroxide solution (6 percent) and the mixture is allowed to act on blonde human hair for 30 minutes. It is then rinsed with water and dried. An extraordinarily intensive brilliant incandescent red is obtained.

Example 3

Hair dye cream

| | |
|---|---|
| 1.0 g | 5-amino-2-methylphenol |
| 0.6 g | 4-amino-3-methylphenol |
| 0.4 g | 2,5-diaminotoluene sulfate |
| 0.3 g | sodium hydroxide, solid |
| 1.0 g | 4-(2'-hydroxyethyl)-amino-1,2-methylenedioxybenzene hydrochloride |
| 0.4 g | sodium sulfite |
| 3.5 g | lauryl alcohol diglycolethersulfate sodium salt, 28 percent aqueous solution |
| 15.0 g | cetyl alcohol |
| 10.0 g | ammonia, 25 percent aqueous solution |
| 68.7 g | water |
| 100.0 g | |

50 g of this hair dye composition is mixed with 50 ml hydrogen peroxide solution (6 percent) shortly before using and the mixture is then applied to light-blond human hair. After it is allowed to act for 30 minutes at 40° C., it is rinsed with water and dried. The hair is dyed a mahogany shade.

We claim:

1. Composition for the oxidative dyeing of hair based upon a combination of coupler substance and developer substance, comprising
   (A) 0.1 to 5.0 percent by weight 5-amino-2-methylphenol or a physiologically compatible salt thereof as coupler substance and
   (B) 0.1 to 4.0 percent by weight 4-amino-3-methylphenol or a physiologically compatible salt thereof and
   (C) 0.1 to 2.0 percent by weight 1,4-diaminobenzene, 2,5-diaminotoluene or a mixture of 1,4-diaminobenzene and 2,5-diaminotoluene or physiologically compatible salts thereof as developer substance, whereby the weight percents are in proportion to the total weight of the composition.

2. The composition according to claim 1, characterized in that component (A) is contained in a quantity of 0.2 to 3.5 percent by weight.

3. The composition according to claim 1, characterized in that component (B) is contained in a quantity of 0.2 to 3.0 percent by weight.

4. The composition according to claim 1, characterized in that the component (C) is contained in a quantity of 0.2 to 1.0 percent by weight.

5. The composition according to claim 2, characterized in that component (B) is contained in a quantity of 0.2 to 3.0 percent by weight.

6. The composition according to claim 1, characterized in that the total quantity of the combination of coupler substances and developer substances is 0.3 to 6.0 percent by weight.

7. The composition according to claim 1, characterized in that the total quantity of combination of coupler substance and developer substance is 0.4 to 5.0 percent by weight.

8. The composition according to claim 1, further comprising an effective amount of a coupler substances selected from the group consisting of 4-(2,-hydroxyethyl)amino-1,2-methylenedioxybenzene, 4-amino-1,2-methylenedioxybenzene, 4-hydroxy-1,2-methylenedioxybenzene, resorcinol, 4-chlororesorcinol, 2-methylresorcinol, 3-aminophenol, sesamol and 3,4-methylenedioxyaniline.

9. The composition according to claim 1, further comprising an effective amount of a direct dyestuff selected from the group consisting of Diamond Fushine (C.I. 42510), Leather Ruby HF (C.I. 42520), 1,4-diamino-2-nitrobenzene, 2-amino-4-nitrophenol, 2-amino-5-nitrophenol, Acid Brown 4 (C.I. 14805), Acid Blue 135 (C.13385), Disperse Red 15 (C.I. 60710), Disperse Violet 1 (C.I. 61100), 1,4,5,8-tetraaminoanthraquinone and 1,4-diaminoanthraquinone.

10. The composition according to claim 1, further comprising an effective amount of an antioxidant selected from the group consisting of sodium sulfite, resorcinol and ascorbic acid.

* * * * *